(12) United States Patent
Chiari et al.

(10) Patent No.: US 10,906,118 B2
(45) Date of Patent: Feb. 2, 2021

(54) WELDING TOOL FOR PERFORMING SMAW OR MIG WELD WITH MANTENANCE OF A CONSTANT DISTANCE BETWEEN THE ELECTRODE AND THE WELD AREA

(71) Applicant: Nuovo Pignone Srl, Florence (IT)

(72) Inventors: Francescosaverio Chiari, Florence (IT); Mario Milazzo, Florence (IT); Marco Magnasco, Florence (IT); Cesare Stefanini, Florence (IT); Francesco Inglese, Florence (IT)

(73) Assignee: NUOVO PIGNONE SRL, Florence (IT)

( * ) Notice: Subject to any disclaimer, the term of this patent is extended or adjusted under 35 U.S.C. 154(b) by 524 days.

(21) Appl. No.: 15/529,770

(22) PCT Filed: Nov. 25, 2015

(86) PCT No.: PCT/EP2015/077591
§ 371 (c)(1),
(2) Date: May 25, 2017

(87) PCT Pub. No.: WO2016/083429
PCT Pub. Date: Jun. 2, 2016

(65) Prior Publication Data
US 2017/0326671 A1 Nov. 16, 2017

(30) Foreign Application Priority Data

Nov. 27, 2014 (IT) .......................... MI2014A002040

(51) Int. Cl.
*B23K 9/12* (2006.01)
*B23K 9/16* (2006.01)
(Continued)

(52) U.S. Cl.
CPC .................. *B23K 9/12* (2013.01); *A61F 9/06* (2013.01); *B23K 9/0008* (2013.01);
(Continued)

(58) Field of Classification Search
CPC ...... B23K 9/0008; B23K 9/124; B23K 9/167; B23K 9/296; B23K 9/164; B23K 9/0953; B23K 9/12; B23K 9/293; A61F 9/06
(Continued)

(56) References Cited

U.S. PATENT DOCUMENTS 3,030,489 A 4/1962 Schaefer et al.
3,261,961 A * 7/1966 Spark .................... B23K 9/291
219/75

(Continued)

FOREIGN PATENT DOCUMENTS

CA 2 485 302 A1 6/2005
CN 200957488 Y 10/2007
(Continued)

OTHER PUBLICATIONS

Chiari, F., et al., Handling Apparatus for Performing a Tig Weld, GE Co-Pending Application No. MI2014A002041, GE Docket No. 278995A-1, filed Nov. 27, 2014.
(Continued)

Primary Examiner — Dana Ross
Assistant Examiner — Kuangyue Chen
(74) Attorney, Agent, or Firm — Baker Hughes Patent Org.

(57) ABSTRACT

A welding tool comprises a main body; a handle attached to the main body to be held by a welder; an electrode attached to the main body; an adjusting device for moving the consumable electrode forward/backward with respect to the main body; a control unit is connected to the adjusting device and is configured to act on the adjusting device for
(Continued)

maintaining a substantially constant distance between the electrode and a weld area.

14 Claims, 10 Drawing Sheets

(51) Int. Cl.
    *B23K 9/095*     (2006.01)
    *B23K 9/29*     (2006.01)
    *A61F 9/06*     (2006.01)
    *B23K 9/00*     (2006.01)
    *B23K 9/167*     (2006.01)

(52) U.S. Cl.
    CPC ............ *B23K 9/0953* (2013.01); *B23K 9/124* (2013.01); *B23K 9/164* (2013.01); *B23K 9/167* (2013.01); *B23K 9/293* (2013.01); *B23K 9/296* (2013.01)

(58) Field of Classification Search
    USPC .......................................................... 219/74
    See application file for complete search history.

(56) References Cited

U.S. PATENT DOCUMENTS

| | | | |
|---|---|---|---|
| 6,242,711 B1* | 6/2001 | Cooper | A61F 9/06 219/130.01 |
| 2006/0075724 A1* | 4/2006 | Kammler | B29C 65/18 53/451 |
| 2009/0276930 A1* | 11/2009 | Becker | A61F 9/06 2/8.2 |
| 2010/0314370 A1 | 12/2010 | Granato, Jr. | |
| 2012/0180180 A1 | 7/2012 | Steve et al. | |
| 2013/0233887 A1* | 9/2013 | Ford | B67D 1/0039 222/129.1 |
| 2014/0311336 A1* | 10/2014 | Berning | F16J 3/02 92/96 |
| 2014/0367366 A1* | 12/2014 | Bertram | B23K 35/38 219/74 |
| 2015/0048057 A1* | 2/2015 | Wada | B23K 9/167 219/75 |

FOREIGN PATENT DOCUMENTS

| | | |
|---|---|---|
| CN | 201913352 U | 8/2011 |
| JP | S5788978 A | 6/1982 |
| JP | H1152755 A | 2/1999 |
| JP | H-11179541 A | 7/1999 |
| JP | H11267922 A | 10/1999 |
| JP | 2001-129666 A | 5/2001 |
| JP | 2001129666 A * | 5/2001 |
| WO | 2012066135 A1 | 5/2012 |

OTHER PUBLICATIONS

Chiari, F., et al., Welding Assistance Device, GE Co-Pending Application No. MI2014A002042, GE Docket No. 278995B-1, filed Nov. 27, 2014.

Search Report and Written Opinion issued in connection with corresponding IT Application No. MI2014A002040 dated Aug. 24, 2015.

International Search Report and Written Opinion issued in connection with corresponding PCT Application No. PCT/EP2015/077591 dated Feb. 10, 2016.

International Preliminary Report on Patentability issued in connection with corresponding PCT Application No. PCT/EP2015/077591 dated May 30, 2017.

Machine Translation and First Office Action and Search issued in connection with corresponding CN Application No. 201580064731.5 dated Dec. 25, 2018.

* cited by examiner

WELDING TOOL FOR PERFORMING SMAW OR MIG WELD WITH MANTENANCE OF A CONSTANT DISTANCE BETWEEN THE ELECTRODE AND THE WELD AREA

BACKGROUND

The subject matter of the present disclosure relates to a welding tool and an arc welding kit, namely, a set of tools that is used to perform a manual arc welding operation.

A known arc welding kit comprises a welding mask and a welding tool. The welding tool comprises an electrode. During welding operations, an electric arc develops between the electrode and the welding area.

In a first and second type of arc welding, the SMAW (Shielded Metal Arc Welding) and the MIG (Metal Inert Gas), the electrode itself melts due to the heat developed by the electric arc, thus becoming the filler material in the weld.

In a third type of arc welding, the TIG (Tungsten Inert Gas), the electrode is solid, and the filler material is provided separately.

With more detail, the kit comprises a set of sensors which can detect the main operating parameters of a welding process, namely the voltage (V), the current (A), the welding speed (W) and their combination to calculate the heat input. The welding mask can be provided with a display device so that these parameters can be shown to a welder, thereby providing him with a possibility of correcting the welding in real time. An example of this welding mask is the one shown in the U.S. Pat. No. 6,242,711 B1.

A disadvantage of the known welding kit is that it merely provides the welder with the welding parameters. However, this does not guarantee that the welder is able to adapt and correct a welding that is being performed improperly. In other words, the welding operation itself still relies heavily on the manual skill of the welder. This is particularly true with respect to the welding voltage, since it is mainly determined by the distance of the electrode from the weld area, thus the work piece.

BRIEF DESCRIPTION OF THE INVENTION

An embodiment of the invention therefore relates to a welding tool. The welding tool comprises a main body. A handle is attached to the main body, and is configured to be held by a welder. An electrode is also provided, and is in particular inserted into the main body. An adjusting device is associated with the electrode for moving it forward/backward with respect to the main body. A control unit is connected to the adjusting device. The control unit is configured to act on the adjusting device for maintaining a substantially constant distance between the electrode and a weld area. The electrode being consumable for performing a SMAW or a MIG weld.

In an embodiment, the welding tool is able to compensate the variation of the distance of the electrode from the weld area. Therefore, even if the welder is somewhat less skilled, the welding can still be performed adequately, as tests have shown. Also, this system is able to compensate small distance variation due to the physiologic tremor of the hand even better than a skilled welder, thus leading to an overall quality improvement of the weld.

Alternatively, the electrode is non-consumable, thereby enabling the welder to perform a TIG weld. In other words, in this case the welding tool is a TIG welding torch.

Another embodiment of the invention relates to an arc welding kit, which comprises the welding tool. The kit also comprises a welding mask. A welding velocity sensor is attached on the welding mask. The welding velocity sensor is configured to detect a welding velocity and to emit a welding velocity signal representing a value of the welding velocity. The control unit comprises a processing module which is configured to compute a velocity difference between the welding velocity and a target velocity value for the welding velocity. The processing module is also configured to emit a velocity difference signal representing the result of the velocity difference. The welding mask comprises a visualization device which is configured to acquire the velocity difference signal and to show a representation of the velocity difference and of consequent heat input difference to a welder.

In this way, an embodiment of the welder has also a feedback on the welding velocity which, in addition to a constant current and to a stable voltage, greatly improves the overall quality of the weld allowing to respect target heat input.

BRIEF DESCRIPTION OF THE DRAWINGS

Further details and specific embodiments will refer to the attached drawings, in which.

DETAILED DESCRIPTION

The following description of exemplary embodiments refer to the accompanying drawings. The same reference numbers in different drawings identify the same or similar elements. The following detailed description does not limit the invention. Instead, the scope of the invention is defined by the appended claims.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

With reference to the attached drawings, with the number 1 is indicated an arc welding kit according to an embodiment of the present invention.

Figure 1:
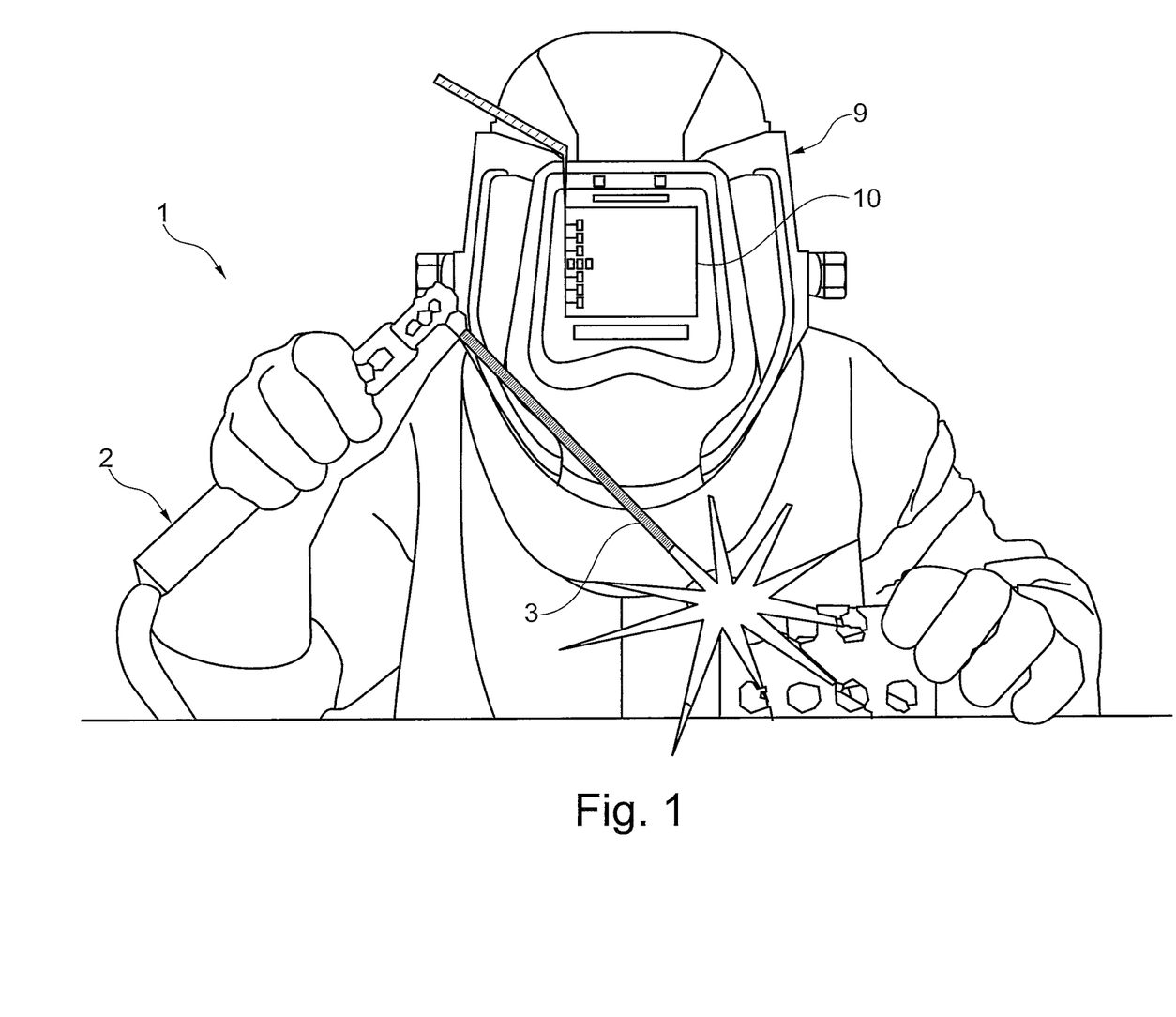
FIG. 1 is a schematic representation of an arc welding kit according to an embodiment.

The welding kit 1 comprises a welding tool 2, which is configured to be held by a welder.

Figure 3:
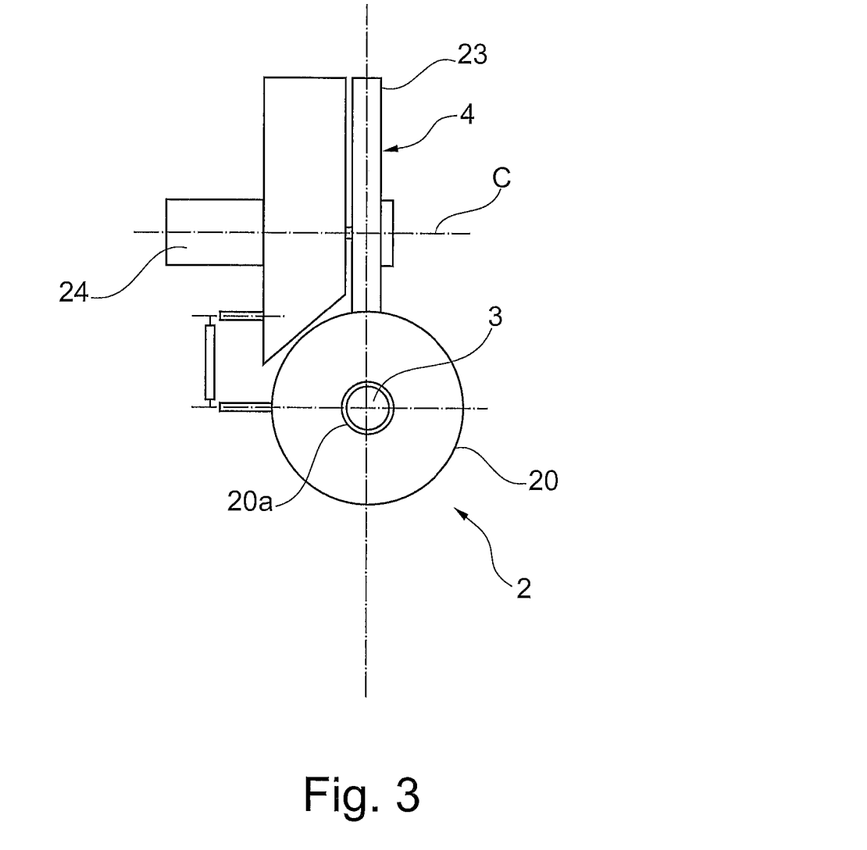
FIG. 3 is a front sectional view of the welding tool of FIG. 2.
Figure 4:
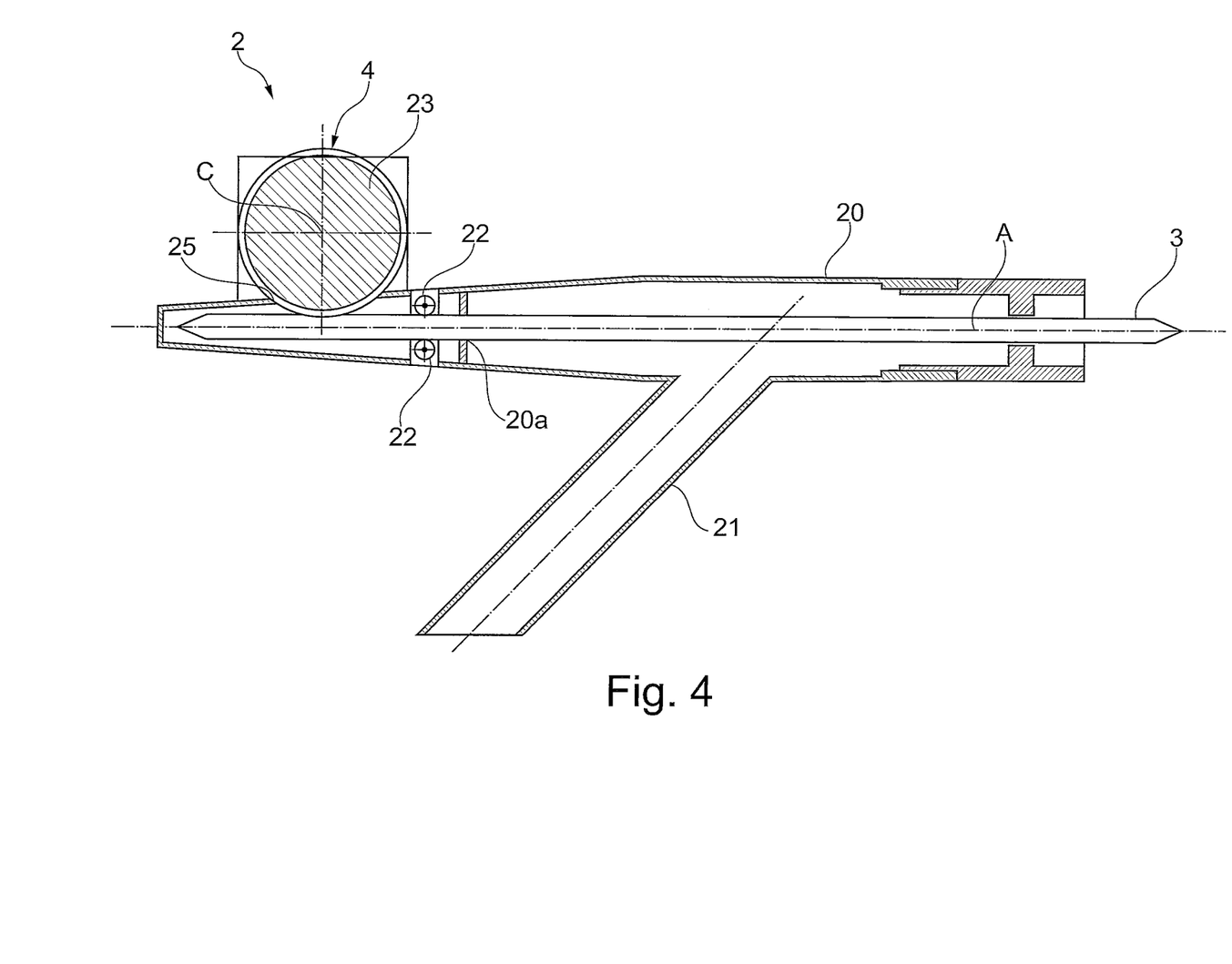
FIG. 4 is a side sectional view of a welding tool according to a further embodiment.

The welding tool 2 comprises an electrode 3. In one embodiment, which is used to perform a SMAW (shielded metal arc weld) or a MIG (Metal Inert Gas), shown in FIGS. 2 and 3, the electrode 3 is consumable. In other words, in this embodiment the electrode 3 becomes the filler material of the weld. Alternatively, as shown in FIG. 4, the electrode 3 is non-consumable, thus it is used to perform a TIG (Tungsten Inert Gas) weld.

Figure 2:
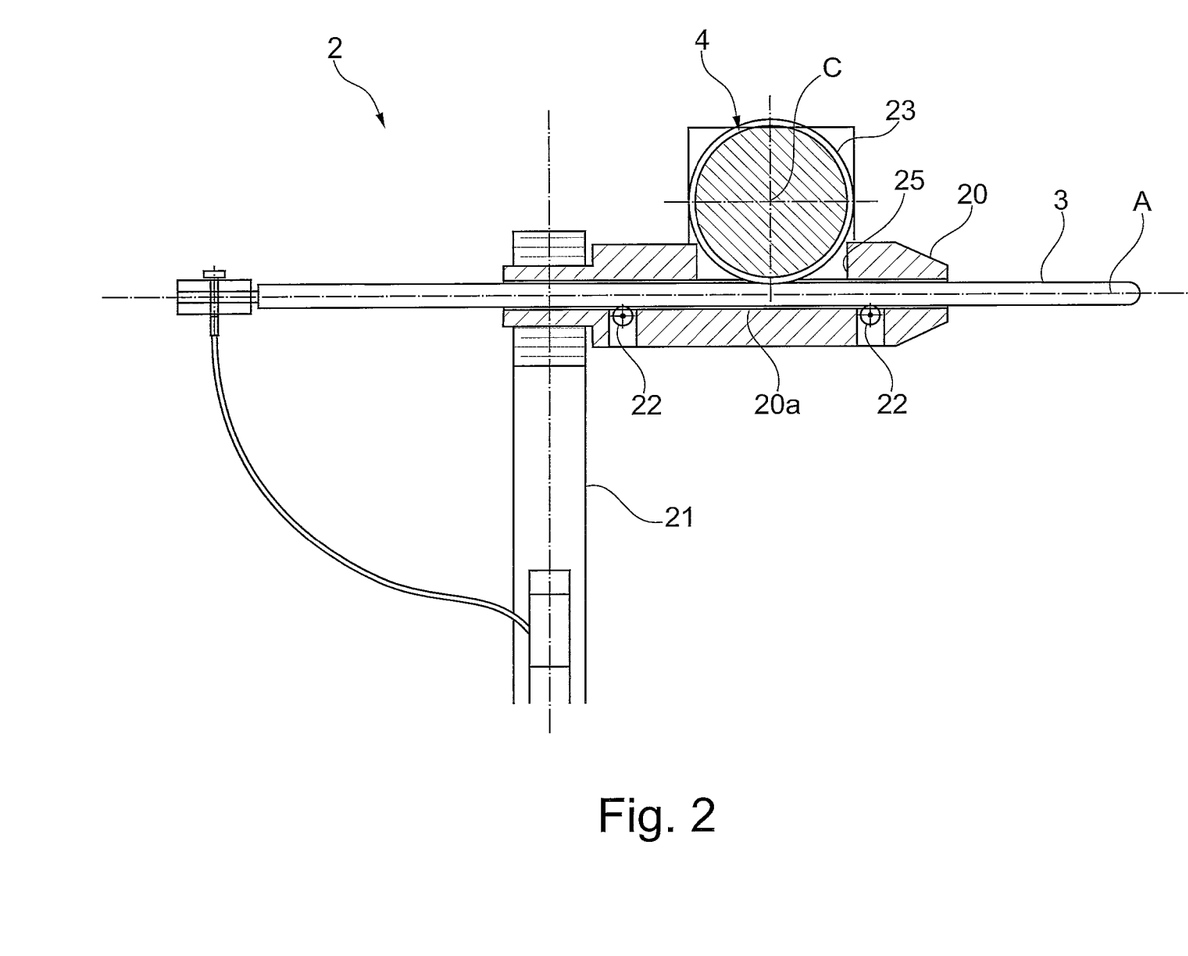
FIG. 2 is a side sectional view of a welding tool according to an embodiment.

With additional details, the welding tool 2 comprises a main body 20, configured to support the electrode 3. The main body 20 is, in an embodiment, axial-symmetric, and develops mainly along a longitudinal axis "A". A handle 21 for the welder supports the main body 20.

The main body 20 has a seat 20a in which the electrode 3 is installed. As shown in FIGS. 2 and 4, the welding tool 2 is provided with bearings 22, which are attached to the main body and located in proximity of the seat 20, so that they can support the electrode 3 and allow it to move forward and backward. In other words, the electrode 3 can move forward and backward inside the seat 20a by sliding on the bearings 22.

Also, the welding tool 2 comprises an adjusting device 4 associated with the electrode 3, in order to move the electrode forward/backward with respect to the main body 20. The adjusting device 4 comprises a wheel 23 having a central axis "C" disposed transversally and, in an embodiment, perpendicularly, to the longitudinal axis "A" of the electrode 3, that is parallel to the axis of the main body 20. Indeed, the main body 20 is provided with a port 25 in which the wheel 24 is inserted.

In operation, the rim of the wheel 23 is in contact with the electrode 3 so that the electrode 3 can be moved along the longitudinal axis "A" by a rotation of the wheel 23 along the central axis "C". The adjusting device 4 also comprises a motor 24. Such motor 24 is an electric motor in an embodiment, in further embodiments the motor is an electromagnetic motor, and is installed on the wheel 23 in order to actuate the wheel 23 and through it, the electrode 3.

When the electrode 3 is consumable, the adjusting device 4 is configured for compensating the variation of distance between the electrode 3 and the weld area due to both the consumption of the electrode and the physiologic tremor of welder hand.

This double constant adjustment allows for maintaining a substantially constant distance between the electrode 3 and the weld area, allowing favorable arcing conditions and consequently an improved weld quality.

With particular reference to the SMAW or MIG welding tool 2 of FIG. 2 please note that, in use, the wheel 23 advances overtime since the electrode 3 is consumed during welding. Therefore, the rotation speed of the motor 24 provides an overall forward movement to the electrode, and varies the rotation speed in order to adjust the distance of the tip of the electrode 3 as will be explained in a following part of the disclosure.

Alternatively, in the TIG welding tool 2 of FIG. 4 the electrode 3 is not consumed during welding. Therefore, the wheel 23 is moved only to adjust the distance of the electrode 3.

Also, in the embodiment of FIG. 4 a source of inert gas is present (not shown in the drawings) in order to shield the tip of the electrode 3 and the weld area from atmospheric oxygen. This source of inert gas is by itself known to the person skilled in the art, thus will not be described in detail.

The kit 1 comprises a voltage sensor 5 which is configured to detect a welding voltage "Vw" between the electrode 3 and the weld area, that is function of the distance between the end of the electrode facing the work piece and the weld area of the work piece. The voltage sensor 5 is also configured to emit a voltage signal "Vs", which is representative of a value of the welding voltage "Vw". Such voltage sensor 5 can be of any type known to the person skilled in the art, and therefore will not be described in detail.

The kit 1 also comprises a control unit 6. In the following part of the disclosure, the control unit 6 will be described by subdividing it into a plurality of modules. Such subdivision is done for ease of description only, and in no way, should be considered as reflecting the physical structure of the control unit 6 itself. Rather, each module can be implemented as an electronic circuit on a suitable hardware support, as a software routine, subroutine or library or as both. Each module may reside on a local unit or may be distributed over a network. Also, the modules can communicate with each other either via a suitable wired or wireless protocol.

The control unit 6 comprises a data acquisition module 7, which is configured to acquire the above-mentioned voltage signal "Vw".

The control unit 6 also comprises a memory module 16, which is configured to store a target voltage value "Vt".

The control unit 6 also comprises an input module 17 configured to set said target voltage value "Vt" in said memory module 16. In a particular embodiment of the invention the input module 17 can be a QR code reader. In this way, the voltage "Vt", as well as any other parameter related to the welding process, can be read by the input module 17 on a suitably encoded QR code.

The control unit 6 also comprises a processing module 8, which is configured to output an actuation signal "Sa" function of at least the voltage signal "Vs". Also, the processing module 8 is configured to retrieve the target voltage value "Vt" and to compare it with the welding voltage value "Vw". The actuation signal "Sa" is therefore at least in part directly proportional to the result of such comparison. With additional detail, the processing module 8 may be programmed with a PID (Proportional, Integral and Derivative) logic. Therefore, the actuation signal "Sa" may be the sum of a part directly proportional to the difference between "Vw" and Vt", of a part proportional to the derivative of such difference and of a part proportional to the integral of such difference. Any possible combination can be used, depending on the chosen control strategy. The processing module 8 can also be configured to supply a voltage difference signal "Dv" representing the result of the difference between "Vw" and "Vt".

The control unit 6 also comprises an actuation module 14 connected to the adjusting device 4. The actuation module 14 is configured to operate the adjusting device 4 as directed by the actuation signal "Sa". In particular, the actuation module 14 operates the motor 24 which rotates the wheel 23. Optionally, the welding kit also comprises a welding mask 9. Such welding mask 9 is configured to be worn by a welder during a welding process as a standard safety mask. In particular, the welding mask 9 comprises a darkened window 10 from which the welder may observe the welding process without being blinded by the intense light.

Additionally, the welding mask 9 is provided with a welding velocity sensor 11. The welding velocity sensor 11 is configured to detect a welding velocity "Wa", and to emit a welding velocity signal "Ws" representing a value of the welding velocity "Wa".

Figure 8:
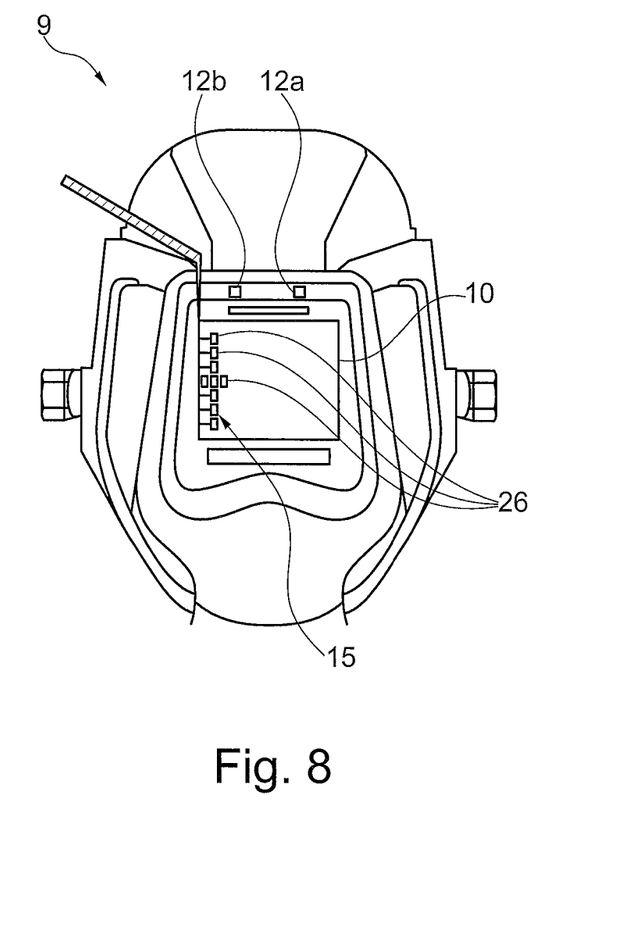
FIG. 8 is a front view of a further component of the kit of FIG. 1.
Figure 9:
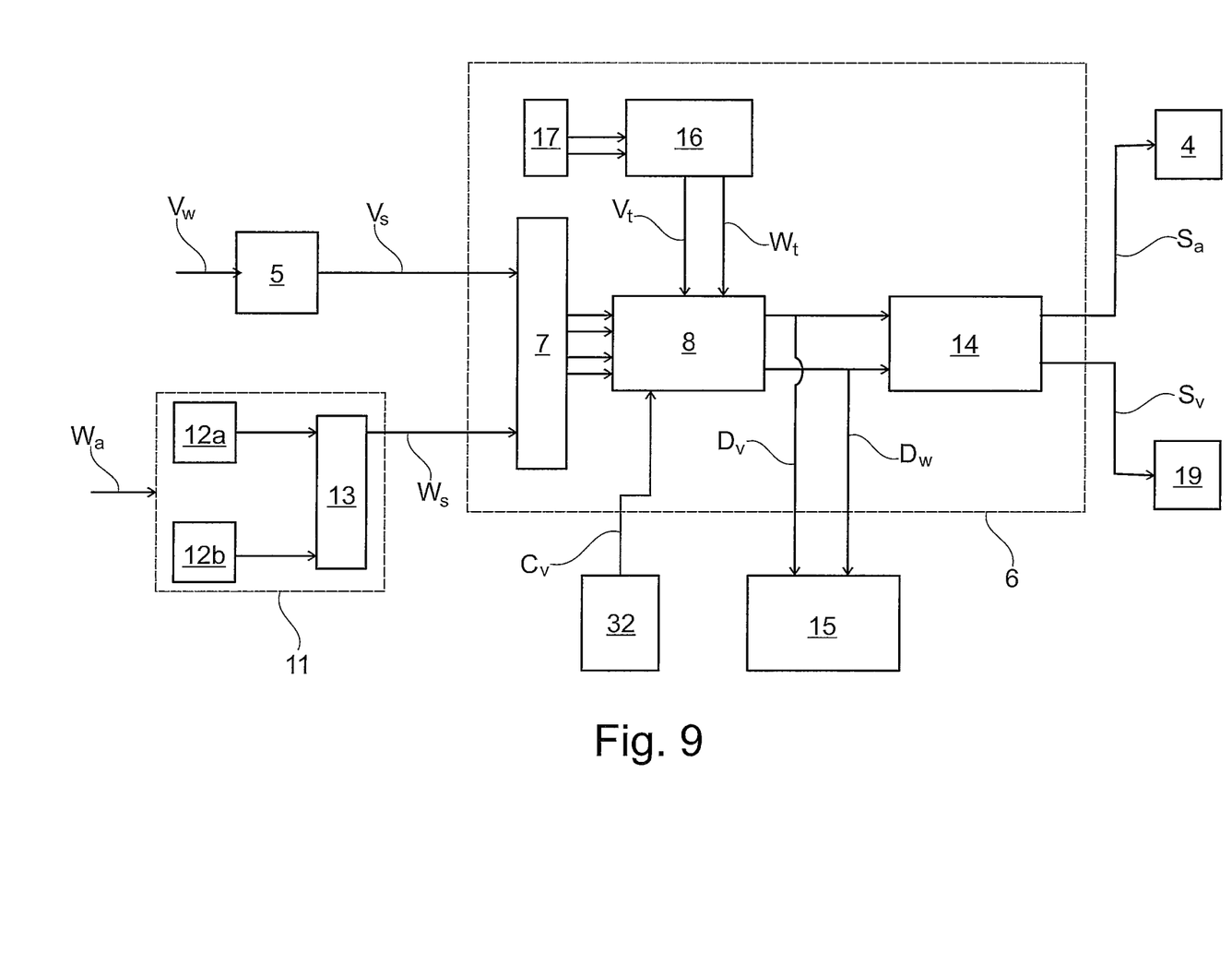
FIG. 9 is a schematic representation of the functioning of the kit of FIG. 1.

According to an embodiment of the invention, the welding velocity sensor 11 comprises a first optical sensor 12a. The first optical sensor 12a is in particular arranged so that, during welding operation it faces the weld area. As shown in FIG. 8, the first optical sensor is placed on the external surface of the welding mask 9 in an embodiment. In further embodiments the first optical sensor is placed over the darkened window 10. The welding velocity sensor 11, in an embodiment, also comprises a reference frame sensor 12b. This reference frame sensor 12b can be any kind of sensor which is able to detect a motion within a fixed frame of reference. For example, the reference frame sensor 12b can be an inertial sensor located on any point of the welding mask 9.

With more detail, in the embodiment shown in FIG. 8 the reference frame sensor 12b is a second optical sensor. The reference frame sensor 12b is therefore arranged to face a fixed reference scene in the environment, as for example the work piece part from the weld area, and placed beside the first optical sensor 12a, in an embodiment. In an embodiment of the invention, the sensors 12a, 12b are imaging cameras.

With additional detail, the first optical sensor 12a is configured to detect the velocity of the welding pool relative to itself. Also, the reference frame sensor 12b is configured to detect the velocity of the above mentioned fixed reference scene. According to one embodiment, the welding velocity sensor 11 also comprises a velocity computing module 13 which is configured to compute the welding velocity "Wa" as a difference between the velocities detected by the second 12b and the first optical sensor 12a. Alternatively, the first optical sensor 12a and reference frame sensor 12b both transmit the respective velocities to the control unit 6, in particular to the data acquisition module 14.

The processing module 8 is also configured to compute a velocity difference between the welding velocity "Wa" and a target velocity "Wt" value, said processing unit being configured to emit a velocity difference signal "Dw" representing the result of said velocity difference.

Optionally, the welding mask 9 comprises a visualization device 15. Such visualization device 15 is arranged to be easily visible by the welder during the welding process. As shown in FIGS. 1 and 8, the visualization device 15 is placed inside the welding mask 9, on one side of the darkened window 10.

With more detail, the visualization device 15 is configured to acquire the above-mentioned velocity difference signal "Dw", thus showing a representation of the velocity difference to the welder. Similarly, the visualization device 15 can be configured to acquire the voltage difference signal "Dv" mentioned above and to show a representation of the voltage difference to the welder.

In an embodiment, the visualization device 15 can be configured to show an operating parameter of the welding process, such as the voltage (V), the current (A), the welding speed (W), respectively between the electrode and the weld area, or their combinations. As shown schematically in FIG. 8, the visualization device comprises a plurality of LEDs 26. These LEDs are arranged in a cross, and are configured to lighten in such a way as to indicate whether the welder should go faster or slower, or if he should get nearer or farther from the weld area.

Figure 5:
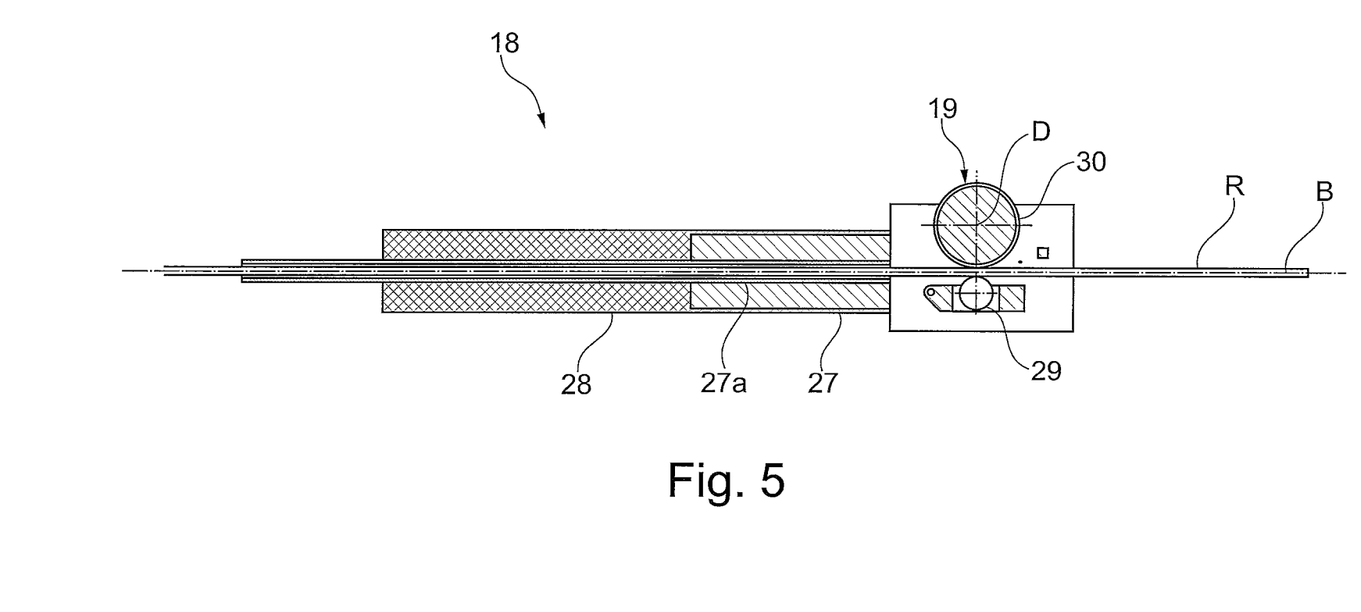
FIG. 5 is a side sectional view of a component of the kit of FIG. 1.
Figure 6:
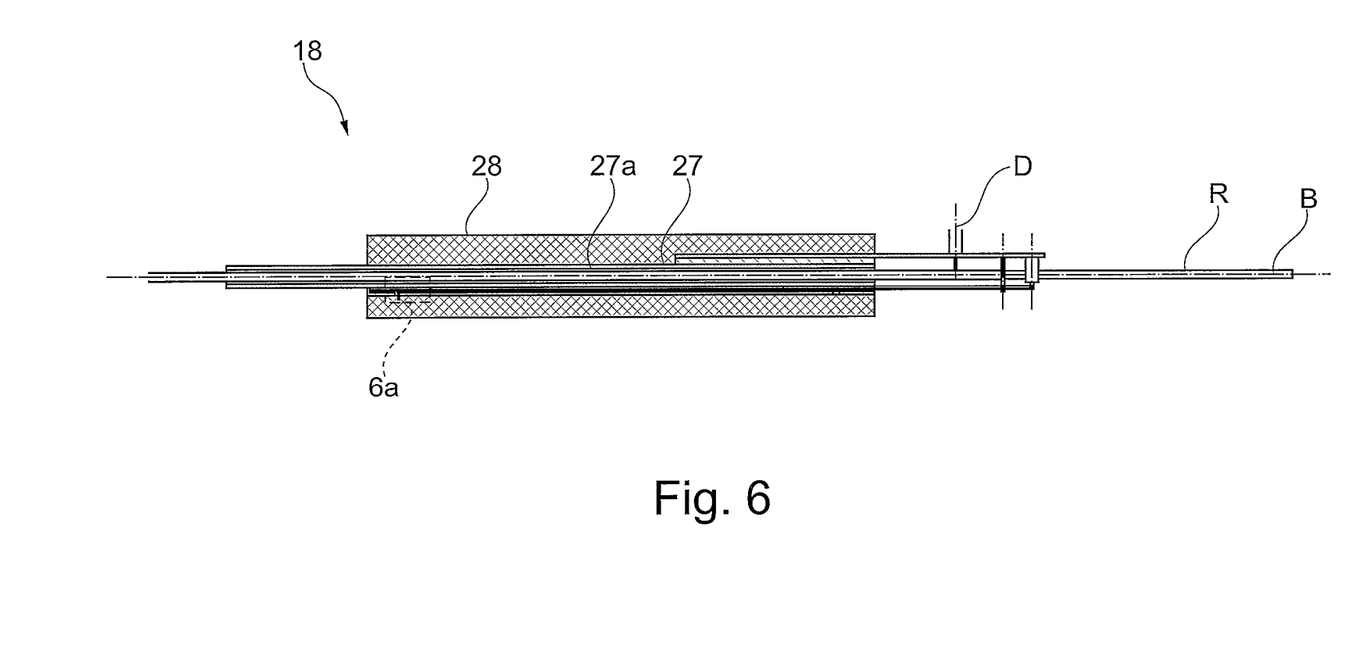
FIG. 6 is a top sectional view of the component of FIG. 5.

Referring specifically to FIGS. 5 and 6, the kit 1 can also comprises a handling apparatus 18 for a filler rod "R". The handling apparatus 18 comprises a feeding device 19 configured to advance the filler rod "R" during welding.

With additional details, the handling apparatus 18 comprises a main body 27, configured to support the filler rod "R". The main body 27 is axial-symmetric, in an embodiment, and develops mainly along a longitudinal axis "B". A handle 28 for the welder is attached to the main body 27. In an embodiment, the handle 28 surrounds the main body 27 of the handling apparatus 18.

The main body 27 has a central seat 27a in which the filler rod "R" is placed. As shown in FIG. 5, the handling apparatus 18 is provided with bearings 29, which are attached to the main body 27 and located in proximity of the central seat 27a, to support the filler rod "R" and allow it to move forward/backward. In other words, the filler rod "R" can move forward/backward inside the seat 27a by sliding on the bearings 29.

The feeding device 19 comprises a wheel 30 having a central axis "D" disposed transversally, and, in an embodiment, perpendicularly to the longitudinal axis "B" of the main body 27.

In operation, the rim of the wheel 30 is in contact with the filler rod "R" so that it can be moved along the longitudinal axis "B" by a rotation of the wheel 30 along the central axis "D". The feeding device 19 also comprises a motor 31. Such motor 31 is electric, in an embodiment and, in further embodiments the motor is linear electromagnetic, and is installed on the wheel 30 in order to actuate the filler rod "R".

In an alternative embodiment, not shown in the drawings, the feeding device 19 comprises an electromagnetic actuation device for the filler rod "R" instead of the wheel 30 and the motor 31.

If the handling apparatus 18 is used, the processing module 8 may be configured to emit a feeding velocity signal "Sv" to the actuation module 14. The feeding velocity signal "Sv" is, in an embodiment, proportional to a feeding velocity value "Fv". The actuation module 14 is therefore also configured to operate the feeding device 19 of the handling apparatus 18 as directed by the feeding velocity signal "Sv".

Figure 6A:
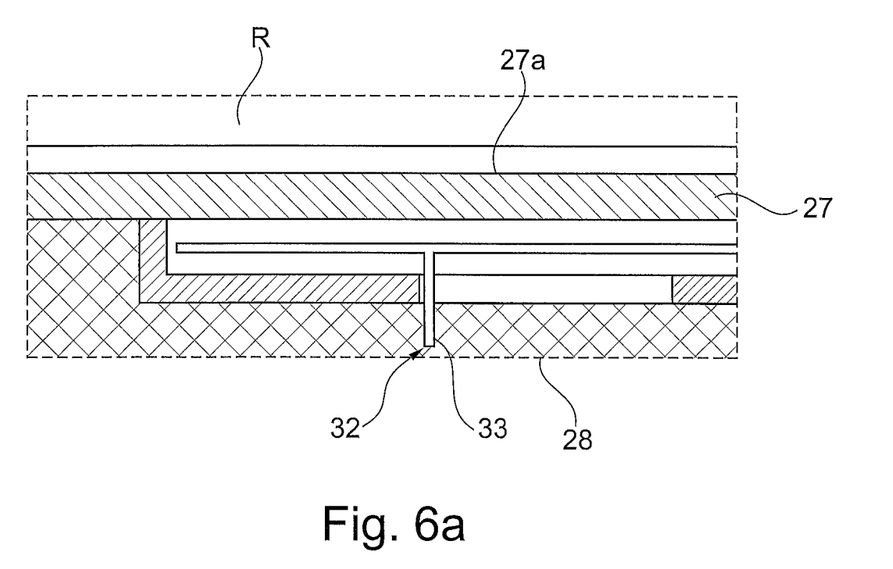
FIG. 6a is an enlarged view of a detail of FIG. 6.
Figure 7:
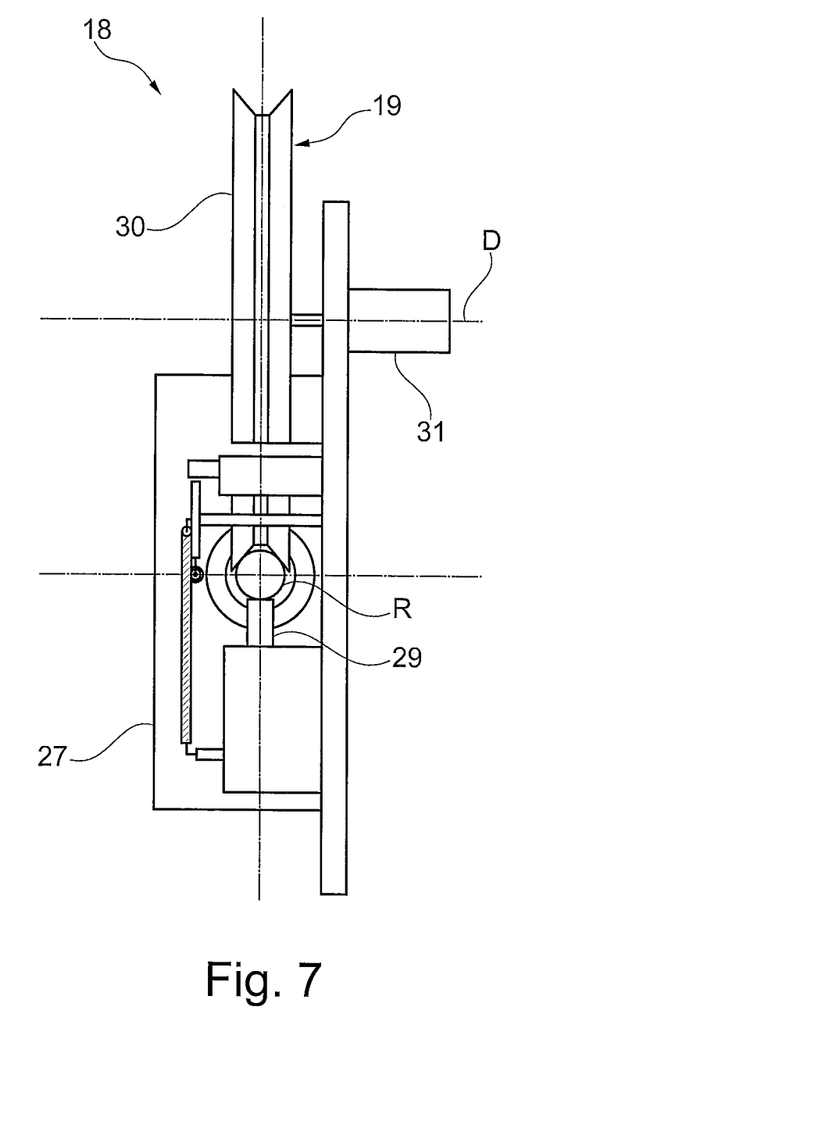
FIG. 7 is a front sectional view of the component of FIGS. 5 and 6.

Also, as shown in FIG. 6a, the handling apparatus 18 comprises a control interface 32 associated with the processing module 8. The control interface 32 is configured to emit a command signal "Cv" to the processing module 8, so that the welder can increase or decrease the feeding velocity signal "Sa".

With additional detail, the control interface 32 comprises a button 33 placed on the handle 28. Specifically, the button 33 allows the welder to adjust the feeding velocity continuously; however, the button 33 is designed as to give a tactile feedback in the form of "clicks" at predetermined intervals so that the welder can be made aware with a certain precision of the amount that the feeding velocity is being manually increased or decreased.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims

The invention claimed is:

1. A welding tool comprising:
   a main body;
   a handle attached to the main body and configured to be held by a welder;
   an electrode;

an adjusting device attached to the main body and comprising a motor to facilitate movement of the electrode forward/backward with respect to the main body;

a control unit connected to the adjusting device and configured to act on the adjusting device for maintaining a substantially constant distance between the electrode and a weld area; and a voltage sensor connected to the control unit and configured to detect a welding voltage between said electrode and the weld area and emit a voltage signal representing a value of the welding voltage, wherein the control unit comprises a processing module configured to output an actuation signal that at least in part is directly proportional to a difference between the welding voltage and a target voltage value, and an actuation module connected to the adjusting device and configured to operate the motor of the adjusting device as directed by the actuation signal.

2. The welding tool according to claim 1, wherein the control unit comprises a data acquisition module configured to acquire the voltage signal.

3. The welding tool according to claim 2, wherein the control unit further comprises a memory module configured to hold the target voltage value, and the processing module is configured to retrieve the target voltage value and to compare it with the welding voltage value.

4. The welding tool according to claim 3, wherein the control unit further comprises an input module configured to set the target voltage value in the memory module.

5. The welding tool according to claim 4, wherein the input module is a QR code reader for reading the target voltage value from a QR code.

6. The welding tool according to claim 1, wherein the adjusting device comprises a wheel driven by the motor and having a central axis disposed transversally to a longitudinal axis of the electrode, the rim of the wheel being in contact with the electrode for moving the electrode forward/backward with respect to the main body.

7. An arc welding kit comprising:
a welding tool according to claim 1;
a welding mask; and
a visualization device attached to the welding mask and arranged to show a representation of an operating parameter of the welding process.

8. The arc welding kit according to claim 7, wherein the welding mask further comprises a welding velocity sensor attached to the welding mask, the welding velocity sensor configured to detect a welding velocity and emit a welding velocity signal representing a value of the welding velocity; and the processing module is further configured to compute a velocity difference between the welding velocity and a target velocity value for the welding velocity and emit a velocity difference signal representing the result of the velocity difference, wherein the visualization device is configured to acquire the velocity difference signal and show a representation of the velocity difference and consequent heat input difference to a welder.

9. The arc welding kit according to claim 7, wherein the processing module is configured to compute a voltage difference between the welding voltage and the target voltage value and emit a voltage difference signal representing the result of the voltage difference, wherein the visualization device is configured to acquire the voltage difference signal and show a representation of the voltage difference to a welder.

10. The welding tool according to claim 6, wherein the central axis disposed perpendicularly to a longitudinal axis of the electrode.

11. The welding tool according to claim 8, wherein the motor is electric.

12. The arc welding kit according to claim 7, wherein the operating parameter of the welding process is selected form the group consisting of voltage, current and welding speed.

13. The welding tool according to claim 1, wherein the adjusting device is further configured to control the rotation speed of the motor.

14. The welding tool according to claim 13, wherein the electrode is consumable, and the adjusting device is further configured to maintain the substantially constant distance between the electrode and the weld area as the electrode is consumed and to compensate for variations in the distance between the electrode and the weld area caused by tremors of a welder's hand.

* * * * *